US00PP34680P3

(12) United States Plant Patent
Gómez Porras et al.

(10) Patent No.: US PP34,680 P3
(45) Date of Patent: Oct. 25, 2022

(54) OLIVE TREE NAMED 'I-16'

(50) Latin Name: ***Olea europaea* L.**
Varietal Denomination: I-16

(71) Applicant: Todolivo S.L., Cordova (ES)

(72) Inventors: Jose María Gómez Porras, Cordova (ES); Luis Rallo Romero, Cordova (ES); Diego Barranco Navero, Cordova (ES); Concepción Muñoz Díez, Cordova (ES); Carlos Trapero Ramírez, Cordova (ES); Pedro Valverde Caballero, Cordova (ES)

(73) Assignee: TODOLIVO S.L., Cordova (ES)

( * ) Notice: Subject to any disclaimer, the term of this patent is extended or adjusted under 35 U.S.C. 154(b) by 0 days.

(21) Appl. No.: 17/376,690

(22) Filed: Jul. 15, 2021

(65) Prior Publication Data

US 2022/0022353 P1 Jan. 20, 2022

(30) Foreign Application Priority Data

Jul. 16, 2020 (ES) ..... 20205555

(51) Int. Cl.
*A01H 5/08* (2018.01)
*A01H 6/00* (2018.01)

(52) U.S. Cl.
USPC ..... Plt./158
CPC ..... *A01H 6/00* (2018.05)

(58) Field of Classification Search
USPC ..... Plt./158
CPC ..... A01H 6/00; A01H 5/08
See application file for complete search history.

*Primary Examiner* — Keith O. Robinson
(74) *Attorney, Agent, or Firm* — Buchanan Ingersoll & Rooney P.C.

(57) ABSTRACT

A new and distinct variety of olive tree, herein referred to by its cultivar name, '1-16', is provided which forms an upright to spreading growth habit. Fruit with a low weight and obtuse shape is produced. The fruit exhibit dark violet coloration and the fruit nipple is absent or weak. The stone of the fruit of the new variety is of medium weight, moderately elongated and possesses a moderately rugose surface.

5 Drawing Sheets

Botanical/commercial classification:
Latin name—*Olea europaea* L.
Common name—Olive tree.
Varietal denomination: 'I-16'.

CROSS-REFERENCE TO RELATED APPLICATIONS

This application claims priority to Spanish Application No. 20205555, which was filed at Spanish Office of Vegetable Varieties in Spain on Jul. 16, 2020, the contents of which are hereby incorporated by reference for all purposes.

SUMMARY OF THE INVENTION

The new variety of olive tree of the present invention was created by a controlled cross in Spain wherein two parents which previously had been studied were crossed in the hope that they would contribute the desired characteristics. The female parent (i.e., seed parent) of the new variety was the 'ARBOSANA' variety (unpatented). The male parent (i.e., pollen parent) was the 'KORONEIKI' variety (unpatented).

The parentage can be summarized as follows:

'ARBOSANA' x 'KORONEIKI'.

The seeds resulting from the above pollination were sown and small plants were obtained which were physically and biologically different from each other. Selective study resulted in the identification of a single plant of the new variety.

The new variety's color is a more intense green when compared to the color of the 'Arbosana' variety. The new variety's size is smaller than the 'Koroneiki' variety. The new variety is different from the 'I-15' variety disclosed in U.S. Plant Pat. No. 32,302 in that it has a longer leaf, higher internode number and a higher canopy density.

It was found that the new variety of the present invention possesses the following combination of characteristics:

(a) the tree has a upright to spreading growth habit
(b) the fruit weight is low and the fruit color is dark violet
(c) the fruit is obtuse and weakly asymmetric
(d) the fruit either possesses a weak or absent nipple
(e) the stone is moderately elongated with a medium weight and moderately rugose surface.

The new variety well meets the needs of the horticultural industry and has not been commercialized. The new variety has an easy agronomic management.

The new variety can be readily distinguished from related similar varieties. For example, the new variety is a small olive cultivar adapted to be cultivated in super high density olive orchards to fulfill the demands of the olive oil sector. In this way, the new variety has a different exact time to ripening, in this case late, different organoleptic characteristics and a different vigor when compared to related varieties since the new variety is specifically cultivated to meet the standards of the olive oil sector. The new variety has a small variety size.

The new variety has been found to undergo asexual propagation in Spain by vegetative cuttings. Asexual propagation by vegetative cutting in Spain has shown that the characteristics of the new variety are stable and are strictly transmissible by such asexual propagation from one generation to another. Accordingly, the new variety undergoes asexual propagation in a true-to-type manner.

The new variety has been named 'I-16'.

BRIEF DESCRIPTION OF THE PHOTOGRAPHS

The accompanying photographs show as nearly true as it is reasonably possible to make the same, in a color illustration of this character, typical specimens of the plant parts of the new variety. The accompanying photographs were taken from a specimen of the new variety that was 3 years old.

DETAILED BOTANICAL DESCRIPTION

Figure 1:
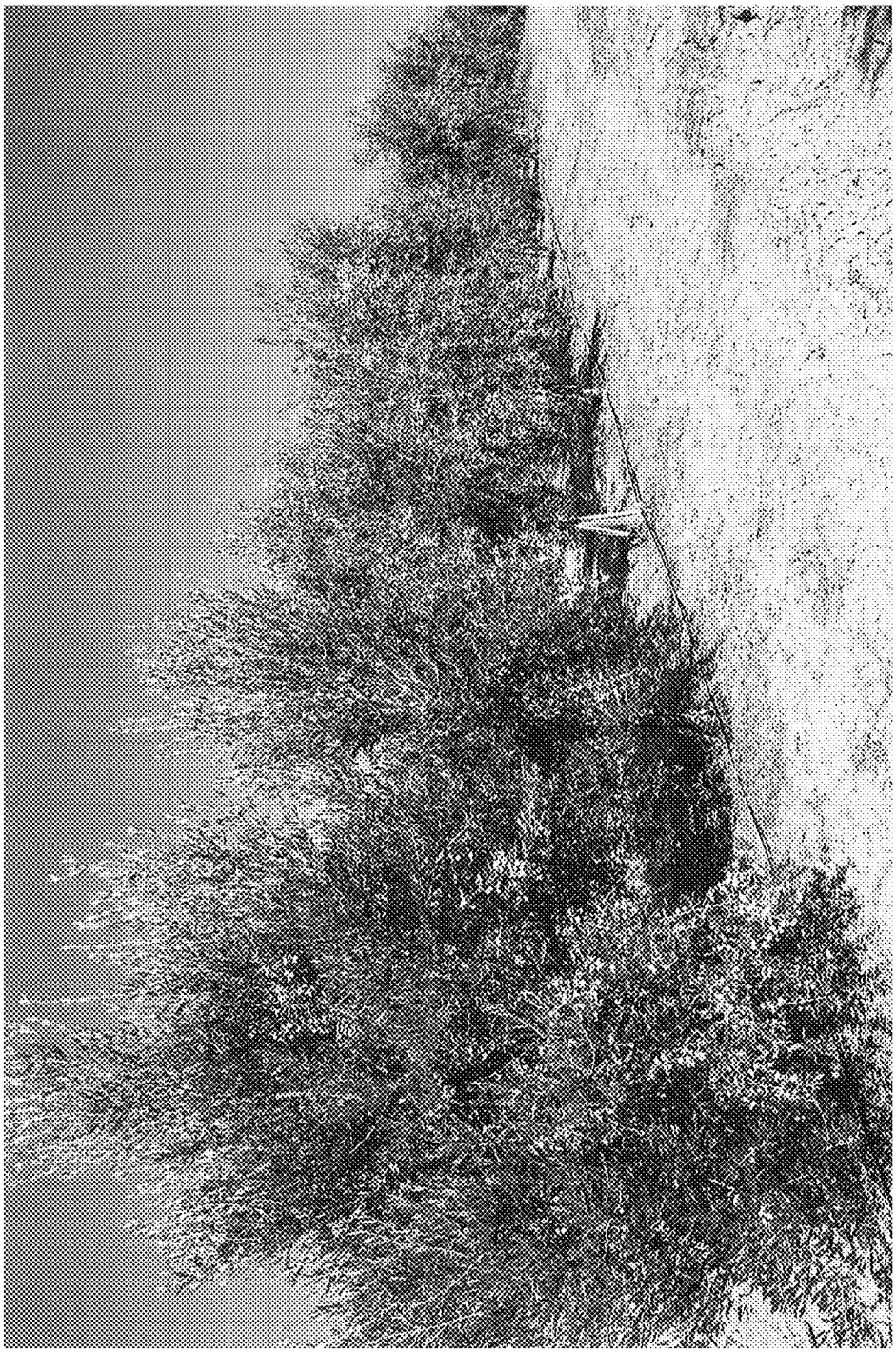
FIG. 1 illustrates the growth of the new variety.
Figure 2:
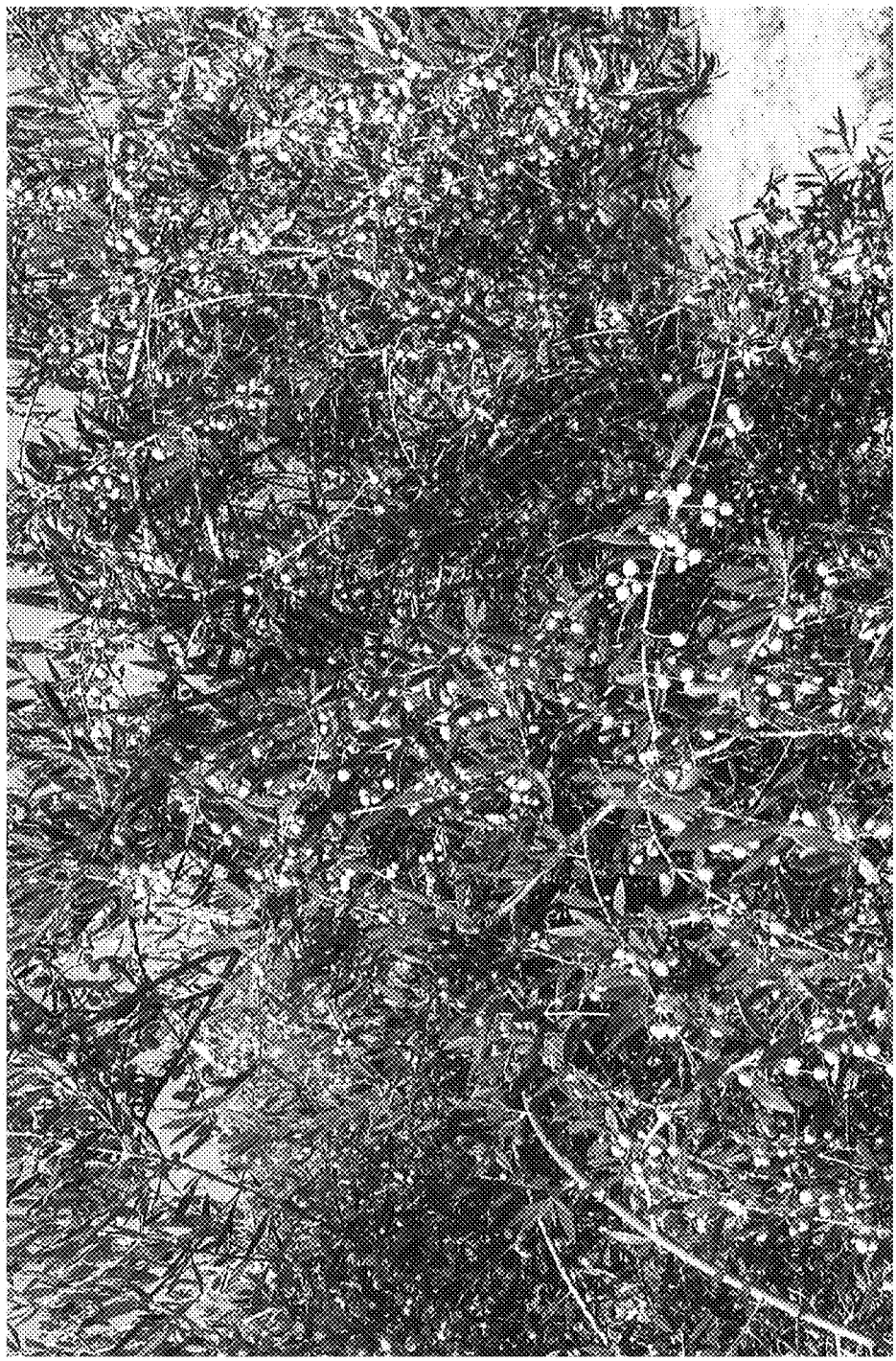
FIG. 2 illustrates the foliage of the new variety.
Figure 3:
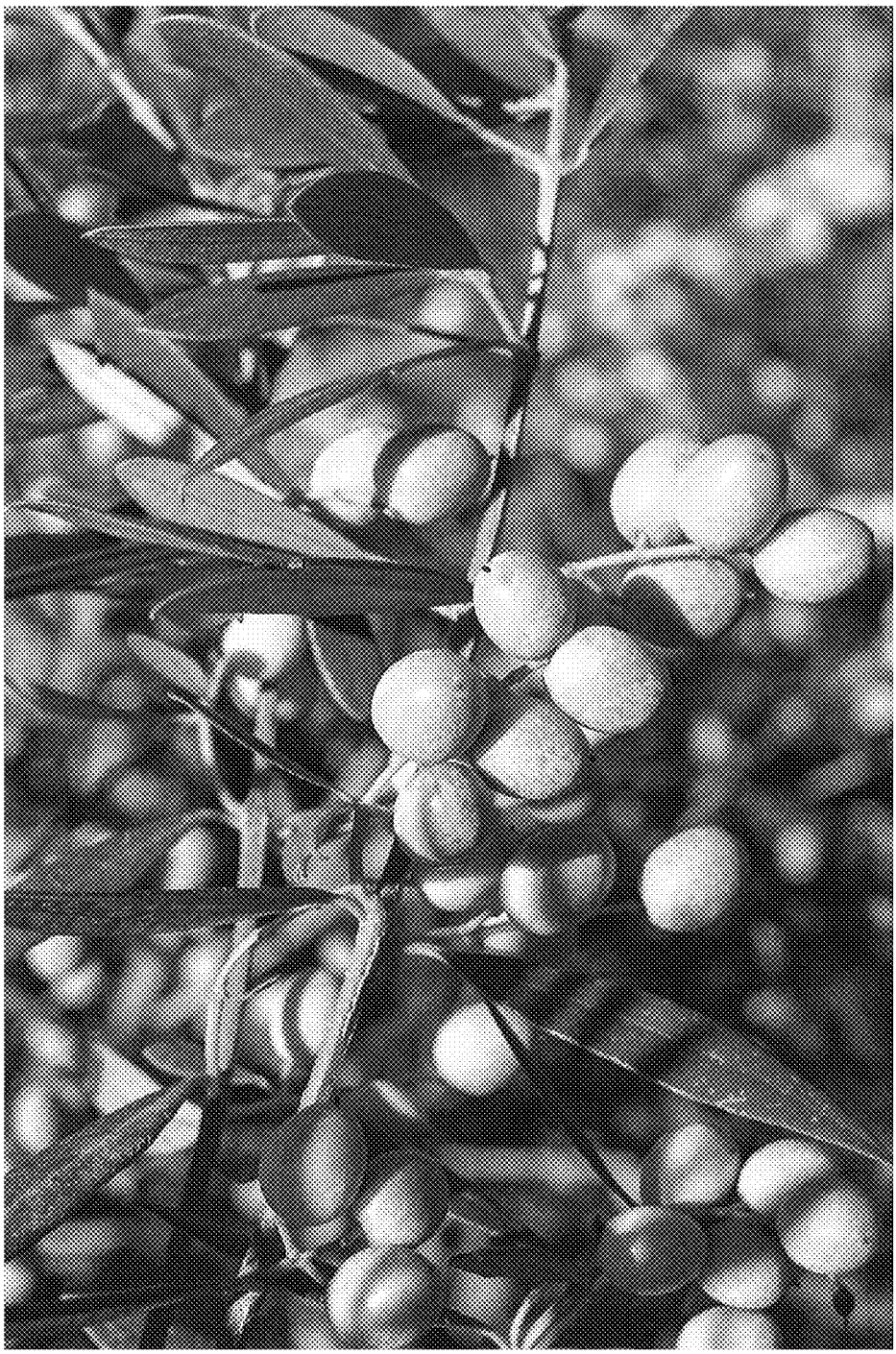
FIG. 3 illustrates specimens of the new variety's immature fruit.
Figure 4:
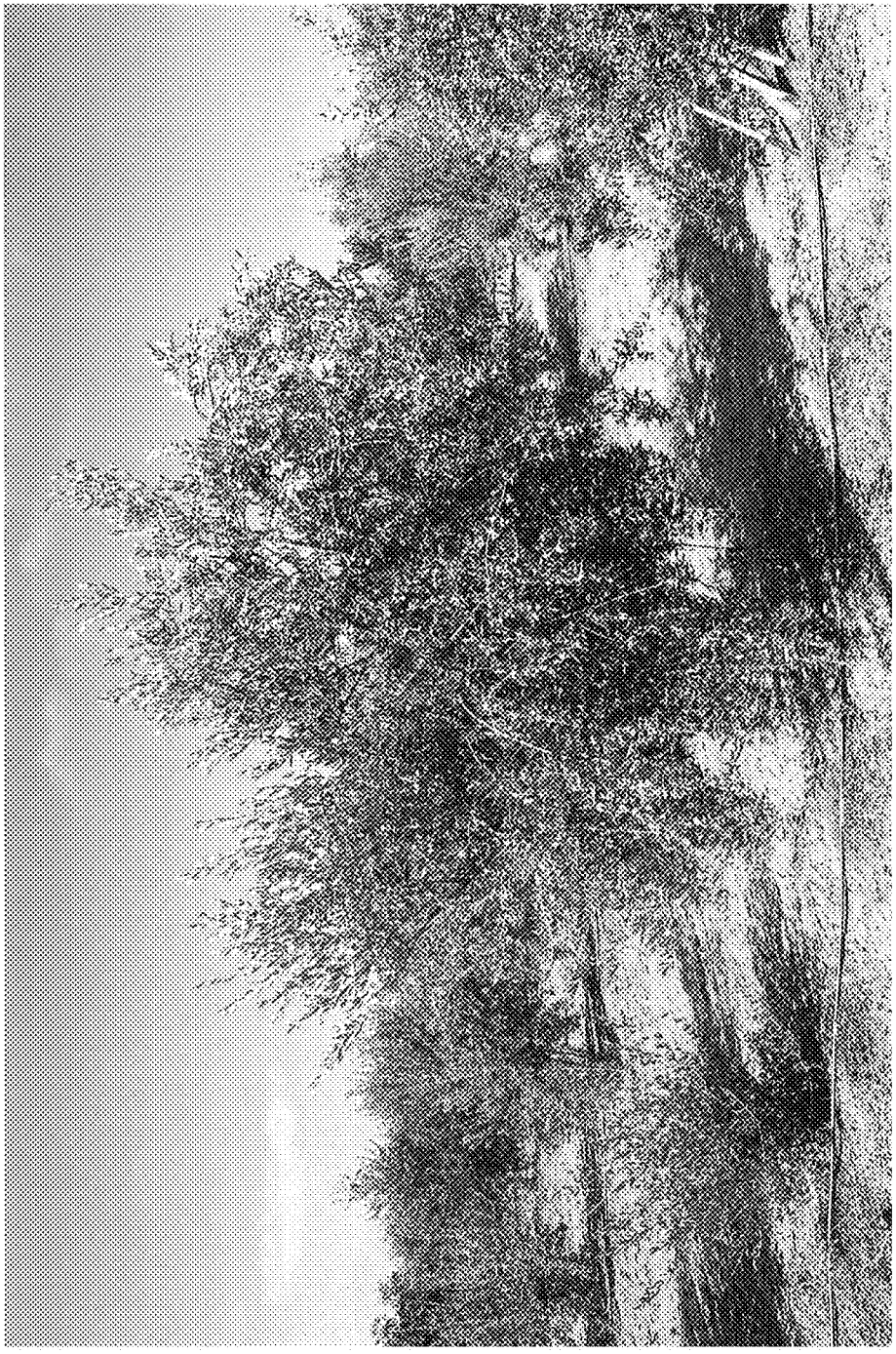
FIG. 4 illustrates the growth habit of the new variety.
Figure 5:
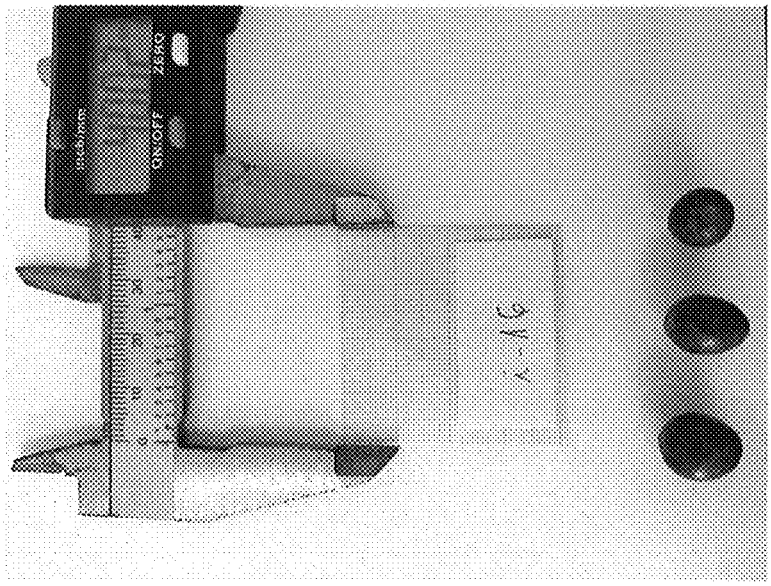
FIG. 5 illustrates the size of the new variety's mature fruit.
Figure 5:
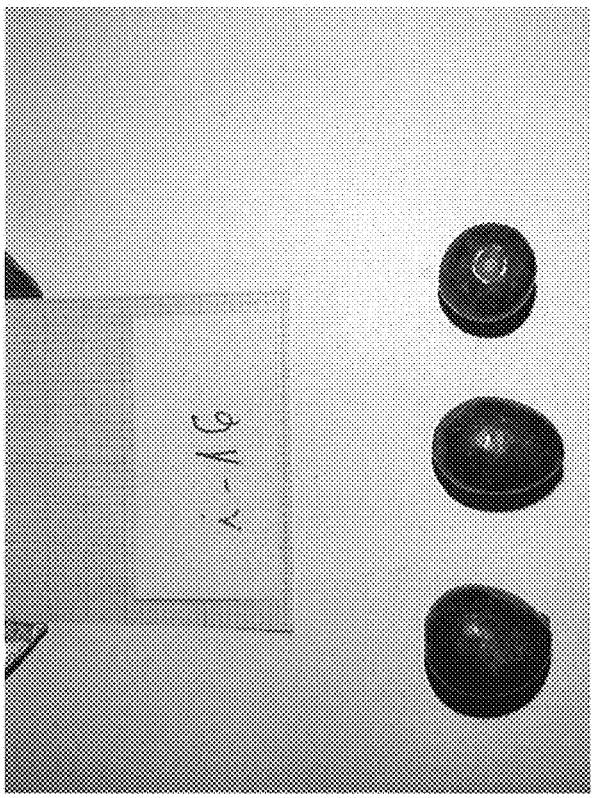

The chart used in the identification of the colors is that of The Royal Horticultural Society (R.H.S. Colour Chart, 2007 edition), London, England. The terminology which precedes reference to the chart has been added to indicate the corresponding color in more common terms. The description is based on data collected from a four-year-old specimen during 2019 in Villafranca (Córdoba, Spain).

Plant:
- *Growth habit*.—Upright to spreading.
- *Vigor*.—Low.
- *Height* (*average*).—216 cm.
- *Width* (*average*).—151 cm.
- *Canopy width*.—151 cm.
- *Canopy density*.—Dense.

Trunk:
- *Surface texture*.—Smooth.
- *Bark color*.—148C (medium brown green).
- *Diameter* (*average*).—55 mm.
- *Cross-section*.—55 mm (diameter).

Main stems:
- *Length* (*average*).—216 cm.
- *Amount of main branches*.—3.
- *Circumference* (*average*).—216 cm.
- *Color designation* (*young stems*).—148C (medium brown green).
- *Color designation* (*mature stems*).—148C (medium brown green).
- *Surface texture* (*young stems*).—Smooth.
- *Surface texture* (*mature stems*).—Smooth.
- *Lenticels*.—Absent.
- *Internode length* (*average*).—10-20 cm.
- *Cross-section*.—55 mm.

Lateral branches:
- *Abundance*.—High.
- *Cross-section*.—15-20 cm.
- *Average length*.—75 cm.
- *Diameter* (*average*).—18 cm.
- *Internode length* (*average*).—9 cm.
- *Texture*.—Smooth.
- *Strength*.—Medium.
- *Color designation* (*young branches*).—148C.
- *Color designation* (*mature branches*).—148C.
- *Fruiting shoots*.—All.
- *Pubescence*.—Absent.

Leaves:
- *Arrangement*.—The arrangement of the leaves is typical of *Olea europaea* L. Species (two opposite leaves per each node).
- *Venation pattern*.—Pinnately parallel.
- *Length* (*average*).—55 mm.
- *Width* (*average*).—10 mm.
- *Color* (*upper surface*) *young leaves*.—142A (light green).
- *Color* (*lower surface*) *young leaves*.—142D (light green).
- *Color* (*upper surface*) *mature leaves*.—143A (medium green).
- *Color* (*lower surface*) *mature leaves*.—142D (light green).
- *Leaf margins*.—Smooth.
- *Texture*.—Smooth.
- *Shape*.—Elongated.
- *Curvature of longitudinal axis*.—None.

Petiole:
- *Average length*.—4-6 mm.
- *Average diameter*.—1 mm.

Inflorescence:
- *Type*.—Racime.
- *Average length*.—Medium.
- *Average width*.—Medium.
- *Number of flowers* (*average*).—At least 15.
- *Flower bud size*.—Medium.
- *Flower bud shape*.—Medium.
- *Flower bud color*.—142D (light green).
- *Flowering time*.—First of May in Villafranca de Córdoba (Córdoba, Spain) during 2 weeks.

Peduncle:
- *Average length*.—3 mm.
- *Average diameter*.—1 mm.
- *Texture*.—Smooth.

Flower:
- *Type*.—In racime.
- *Shape*.—Ovate.
- *Diameter* (*average*).—6 mm.
- *Height* (*average*).—5 mm.
- *Sepals*.—4 sepals in cross (unfused).
- *Sepal length* (*average*).—3 mm.
- *Sepal width* (*average*).—2 mm.
- *Sepal shape*.—Elongated.
- *Sepal base shape*.—Peak.
- *Sepal texture*.—Smooth.

Androcium:
- *Stamen number*.—2.
- *Filament length*.—3 mm.
- *Anther attachment*.—Basifixed.
- *Anther shape*.—Globular (monothecal).
- *Anther length*.—2 mm.
- *Pollen amount*.—Unknown.

Gynoecium:
- *Pistil quantity*.—1.
- *Stigma shape*.—Ovado.
- *Stigma length*.—2 mm.
- *Style length*.—2 mm.
- *Ovary position*.—Superior.
- *Ovary shape*.—Hypoginus.
- *Ovary diameter*.—About 2 mm.
- *Carpels*.—1.

Calyx:
*Number* (*average*).—4.
*Shape*.—In cross shape.
*Base*.—Fused.
*Margin*.—Smooth.
*Texture*.—Smooth.
*Color* (*upper*).—155A (White).
*Color* (*lower*).—155A (White).
Pedicel:
*Length* (*average*).—1-5 mm.
*Diameter* (*average*).—1 mm.
*Color*.—145D (light green).
*Texture*.—Smooth.
Fruit:
*Average weight*.—1.2 g (low).
*Shape*.—Apex obtuse.
*Color designation* (*flesh color*).—59A (light blue Pink).
*Color designation skin color* (*young*).—79A (Dark violet).
*Ripening*.—Late.
*Fat yield*.—18,5.
*Size* (*average*).—Small.
*Length* (*average*).—15.2 mm.
*Width* (*average*).—12 mm.
*Height* (*average*).—15.2 mm.
*Suture*.—Absent.
*Marbling*.—Absent.
*Symmetry*.—Symmetrical.
*Pistil scar*.—Ovate.
*Mucron*.—Present.
*Lenticel size* (*immature fruit*).—Medium (1 mm).
*Number of lenticels* (*immature fruit*).—Slow number of lenticels.
*Nipple*.—Present.
Stalk:
*Length* (*average*).—5 mm.
*Diameter* (*average*.—1 mm.
*Color*.—148C (medium brown green).
*Depth of stalk cavity* (*average*).—2 mm.
Stone:
*Quantity*.—1.
*Shape*.—Moderately elongated.
*Average weight*.—0.22 g (low).
*Average length*.—11.6 mm.
*Average width*.—6.5 mm.
*Grooving*.—7.
*Sutures*.—Medium.
*Color*.—152C (dark green brown).
*Symmetry*.—Symmetrical.
*Texture*.—Moderately rugose.
*Mucron*.—Present.
Development:
*Productivity*.—Very high and constant, 744 oil liter per acre and year.
*Time of flowering*.—First days of May in Villafranca de Córdoba, Spain.
*Flowering period*.—2 weeks.
*Time of fruit ripening*.—3 months.
*Ripening period*.—November-January.
*Winter hardiness/cold tolerance*.—Unknown.
*Drought/heat tolerance*.—Unknown.
*Plant/fruit disease, pest resistance*.—Free of *Cucumovirus cucumber mosaic* virus (CMV), *Nepovirus* cherry leaf roll virus (CLRV), *Incertae Sedis* strawberry latent ringspot virus (SLRSV) and *Nepovirus arabis mosaic* virus (ArMV).

The new 'I-16' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of olive tree named 'I-16', as described and illustrated herein.

* * * * *